United States Patent
Tanaka et al.

(10) Patent No.: US 9,155,464 B2
(45) Date of Patent: Oct. 13, 2015

(54) VISUAL FIELD EXAMINATION SYSTEM

(75) Inventors: Shin Tanaka, Hamamatsu (JP); Satoshi Shimada, Hamamatsu (JP)

(73) Assignee: KOWA COMPANY LTD. (JP)

( * ) Notice: Subject to any disclaimer, the term of this patent is extended or adjusted under 35 U.S.C. 154(b) by 0 days.

(21) Appl. No.: 13/817,884

(22) PCT Filed: Aug. 24, 2010

(86) PCT No.: PCT/JP2010/064207
§ 371 (c)(1),
(2), (4) Date: Feb. 20, 2013

(87) PCT Pub. No.: WO2012/025983
PCT Pub. Date: Mar. 1, 2012

(65) Prior Publication Data
US 2013/0148081 A1    Jun. 13, 2013

(51) Int. Cl.
*A61B 3/10* (2006.01)
*A61B 3/14* (2006.01)
*A61B 3/02* (2006.01)
*A61B 3/024* (2006.01)
*A61B 3/12* (2006.01)

(52) U.S. Cl.
CPC .................. *A61B 3/102* (2013.01); *A61B 3/024* (2013.01); *A61B 3/12* (2013.01)

(58) Field of Classification Search
CPC ........ A61B 3/102; A61B 3/14; A61B 5/0066; A61B 3/0025; A61B 3/1015; A61B 2019/5234; A61B 2576/00; A61B 5/0073; A61B 8/10; A61B 3/024

USPC ........... 351/206, 246, 224; 382/131; 128/922; 600/452, 558
See application file for complete search history.

(56) References Cited

U.S. PATENT DOCUMENTS

| | | | |
|---|---|---|---|
| 6,829,383 B1 * | 12/2004 | Berestov | 382/154 |
| 7,301,644 B2 * | 11/2007 | Knighton et al. | 356/479 |
| 7,364,296 B2 * | 4/2008 | Miller et al. | 351/206 |
| 7,884,945 B2 * | 2/2011 | Srinivasan et al. | 356/497 |
| 2007/0216909 A1 * | 9/2007 | Everett et al. | 356/479 |
| 2007/0263227 A1 * | 11/2007 | Mujat et al. | 356/511 |
| 2007/0276269 A1 * | 11/2007 | Yun et al. | 600/504 |

(Continued)

FOREIGN PATENT DOCUMENTS

| | | |
|---|---|---|
| JP | 2004502483 | 1/2004 |
| JP | 2008 36297 | 2/2008 |

(Continued)

*Primary Examiner* — Scott J Sugarman
*Assistant Examiner* — Collin X Beatty
(74) *Attorney, Agent, or Firm* — Adams & Wilks

(57) ABSTRACT

A visual field examination system measures the visual field of an eye. Quantitative information of a 3D retinal layer structure is acquired by detecting a range in which a peak of a retinal reflectance distribution obtained by OCT scanning is lost. A position of the fovea of the eye fundus is identified based on the acquired information. A location of a range in which the peak of the retinal reflectance distribution is lost is specified in a 2D fundus image based on the position of the fovea, and the specified location is marked on a region of the 2D fundus image. A position of the marked region is detected, and a visual inspection field region is generated based on the detection. Visual field examination points of the visual inspection field region are presented to the eye through a visual field dome for carrying out visual field examination of the eye.

3 Claims, 6 Drawing Sheets

(56) References Cited

U.S. PATENT DOCUMENTS

| | | | |
|---|---|---|---|
| 2007/0285619 A1* | 12/2007 | Aoki et al. | 351/206 |
| 2007/0287932 A1* | 12/2007 | Huang et al. | 600/558 |
| 2008/0100612 A1* | 5/2008 | Dastmalchi et al. | 345/418 |
| 2008/0309881 A1* | 12/2008 | Huang et al. | 351/246 |
| 2009/0073387 A1* | 3/2009 | Meyer et al. | 351/246 |
| 2009/0143685 A1* | 6/2009 | Elner et al. | 600/476 |
| 2009/0268162 A1* | 10/2009 | Stetson et al. | 351/246 |
| 2010/0149489 A1* | 6/2010 | Kikawa et al. | 351/206 |

FOREIGN PATENT DOCUMENTS

| | | |
|---|---|---|
| JP | 2008518740 | 6/2008 |
| JP | 2009 34480 | 2/2009 |
| WO | 02 03852 | 1/2002 |
| WO | 2006052479 | 5/2006 |
| WO | 2008157406 | 12/2008 |

* cited by examiner

VISUAL FIELD EXAMINATION SYSTEM

BACKGROUND OF THE INVENTION

1. Technical Field

The present invention relates to a visual field examination system that is configured using an OCT fundus device, a perimeter and a fundus image-capturing device such as a fundus camera.

2. Background Art

A perimeter having a manual or automatic measurement mode is a conventionally known device for measuring the visual field of an eye under examination. In eye diseases such as glaucoma, for example, symptoms such as constriction of visual field or scotoma are known to take place, and a perimeter is used in the diagnosis of diseases of this type.

This type of perimeter is adapted so that an illumination spot is projected as a stimulus onto a visual field dome having a hemispherical projection surface, and the projection position of the stimulus either is manually controlled or is automatically controlled in accordance with a predetermined program to record a response from the subject at respective projection positions.

If an abnormal position in the retina of an eye under examination can be identified using a two-dimensional fundus image obtained from fundus photography by a fundus camera, it would presumably be useful in diagnosis. Information obtained by comparison with not only the structure but also the function of the retina is believed to be useful in the diagnosis of glaucoma, and accordingly there have been proposed examination systems capable of combining both a fundus image and a measurement result obtained by a perimeter.

At present, there are also known devices such as an OCT (Optical Coherence Tomography) capable of measuring the layer thickness of the retina of an eye under examination. Incorporating the information (hereinafter referred to as an "OCT image", especially for images) which relates to the three-dimensional structure of the retina obtained by this type of device would presumably make even more highly accurate diagnosis of the retina possible.

For example, Patent Document 1 discloses an ophthalmologic information processing device in which light is projected onto the fundus, and light reflected therefrom is detected to acquire a three-dimensional image indicative of the morphology of the retina of an eye under examination on the basis of a detection result using OCT technology in order to calculate the layer thickness of the retina from the three-dimensional image, the information of the retinal layer thickness being compared with the result of a visual field examination carried out in advance, thereby obtaining ophthalmologic information.

Patent Document 2 discloses an ophthalmologic examination system in which a two-dimensional fundus image is combined with a measurement result obtained by a perimeter. In the perimeter of Patent Document 2, a stimulus is presented in a position which lies on a separately captured fundus image and corresponds to a predetermined examination position within a coordinate system of a visual field dome, and the visual field is measured according to a visual response from the subject.

PRIOR ART DOCUMENTS

Patent Documents

Patent Document 1: JP 2009-34480 A
Patent Document 2: JP 2008-36297 A

SUMMARY OF INVENTION

Problems to be Solved by the Invention

Patent Document 1 discloses a technique for incorporating an OCT fundus image into a visual field examination. However, in the described configuration in Patent Document 1, the visual field examination is performed and then the OCT fundus image is acquired to identify a stimulus position within the three-dimensional image of the retina and measure the layer thickness of the retina at that position for comparison with the visual field examination. Therefore, it is necessary to perform an entire visual field examination from the start. The visual field examination must be implemented in all of the ranges without any distinction between normal parts and portions suspected to have a lesion, and therefore it is not an efficient manner of measuring portions suspected to have a lesion in the briefest time possible.

Patent Document 2 discloses a perimeter in which a previously obtained fundus image is used to specify a visual field measurement point for an eye under examination, and discloses a technique for matching together the coordinates of the fundus image and the actual coordinates of the eye under examination. However, information such as OCT relating to the three-dimensional structure of the retina is not used in Patent Document 2, and a two-dimensional fundus image provides no information in the depth direction of the fundus, so that there would not be high accuracy in identifying portions suspected to have a lesion.

In view of the foregoing problems, it is an object of the present invention to provide a visual field examination system useful in ophthalmologic diagnosis in which both a two-dimensional fundus image and information relating to the three-dimensional structure of the fundus of an eye under examination obtained by an OCT device are used to appropriately control a perimeter-assisted visual field examination, thereby making it possible to examine more accurately and in a briefer period of time in comparison to a conventional system.

SUMMARY OF THE INVENTION

In order to solve the foregoing problems, the present invention provides a visual field examination system in which a stimulus is presented at a predetermined position of a visual field coordinate system set on a visual field dome to measure the visual field of an eye under examination, comprising:

a first memory for storing a two-dimensional fundus image of the eye under examination;

a second memory for storing a three-dimensional image of the retina of the eye under examination, the three-dimensional image being acquired by an OCT device;

fovea identifying means for identifying the position of the fovea of the fundus of the eye under examination from quantitative information of a three-dimensional retinal layer structure and from the three-dimensional retinal layer structure, the quantitative information of the three-dimensional retinal layer structure being obtained by means for detecting a peak from the reflectance distribution of the retina obtained by analyzing the three-dimensional image of the retina, and by means for detecting from the reflectance distribution of the retina the disappearance of a peak corresponding to a specific position within the retinal tissue of the eye under examination and for detecting the range of disappearance thereof;

a fundus image position identifying means for identifying, from the positional relationship between the three-dimensional retinal layer structure stored in the first memory and the fovea identified by the fovea identifying means, to which range in the three-dimensional image of the retina the range of disappearance of the peak corresponds; and marking means for marking a predetermined examination point on the two-dimensional fundus image stored in the first memory at a position corresponding to the range of disappearance of the peak identified by the fundus image position identifying means;

wherein a region marked by the marking means is detected to generate, on the basis of the position of the region marked, a visual field examination region including visual field examination points to be presented on the visual field dome, the visual field examination points of the visual field examination region being presented to the subject using the visual field dome to perform a visual field examination for the eye under examination.

According to the above-described configuration, it is possible to appropriately control a perimeter-assisted visual field examination by using a two-dimensional fundus image and information relating to the three-dimensional structure of the fundus of the eye under examination obtained by an OCT device. In particular, it is possible to identify a position suspected to have a lesion or abnormality using the information relating to the three-dimensional structure of the retina obtained by the OCT device, i.e., the information relating to the thickness direction of the retinal layers. Therefore it is possible to accurately identify a visual field examination range on the fundus, and efficiently carry out a visual field examination over a range of the fundus of the eye under examination suspected to have an abnormality. Also, there is not adopted a configuration in which the visual field examination is carried out and then the OCT information is incorporated, but a configuration in which the information relating to the three-dimensional structure of the retina is acquired by OCT and then the visual field examination range on the fundus is narrowed down. This makes it possible to quickly and efficiently carry out the visual field examination for the range of the fundus of the eye under examination suspected to have an abnormality.

DETAILED DESCRIPTION OF THE INVENTION

The present invention will be described with reference to the accompanying drawings based on an embodiment as a mode for carrying out the present invention. Illustrated below is an embodiment relating to a visual field examination system that is configured using an OCT fundus device, a perimeter and a fundus image-capturing device such as a fundus camera.

Embodiment 1

Figure 1:
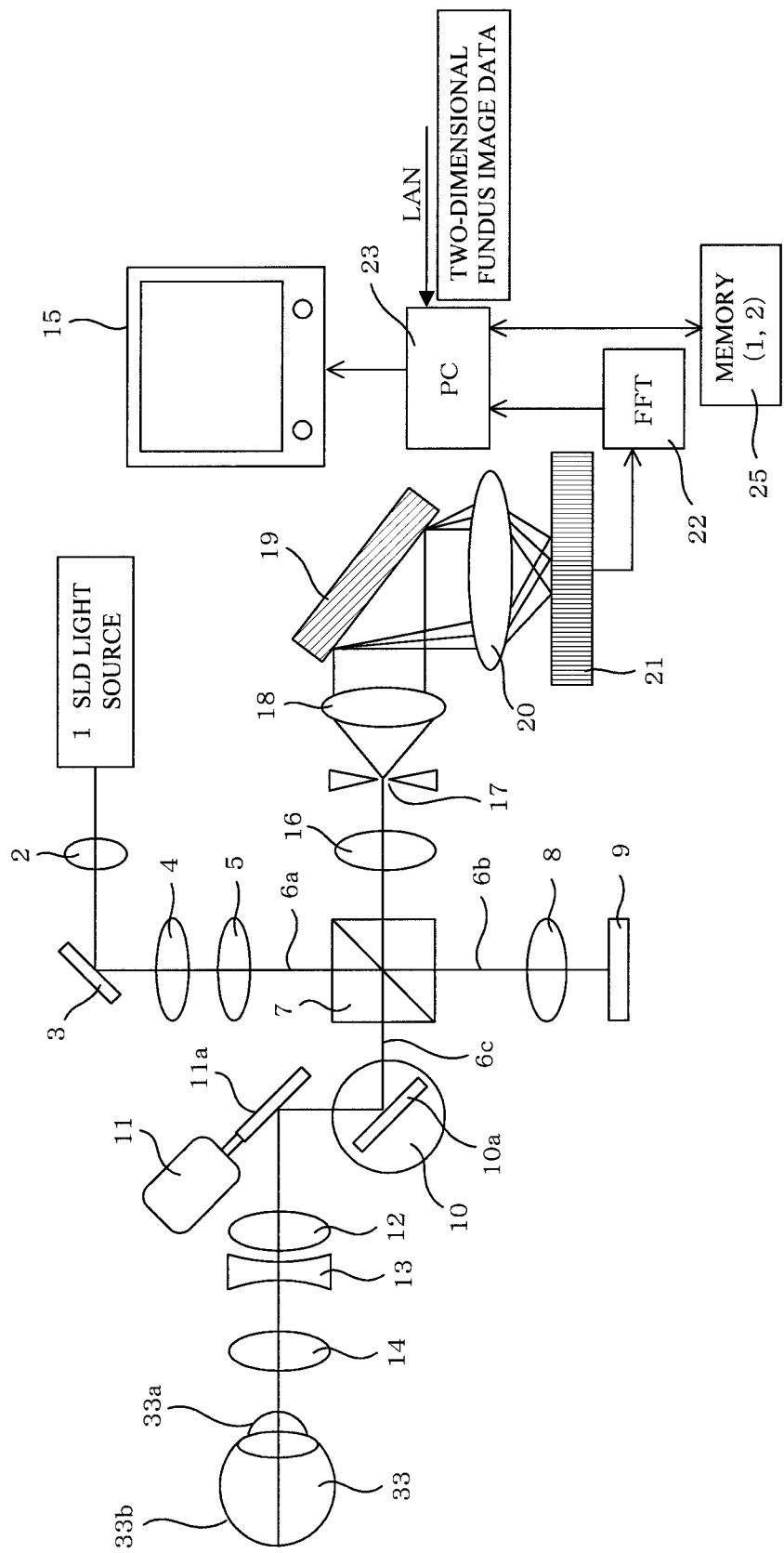
FIG. 1 is a block diagram illustrating a configuration of an OCT fundus device in the present invention.
Figure 2:
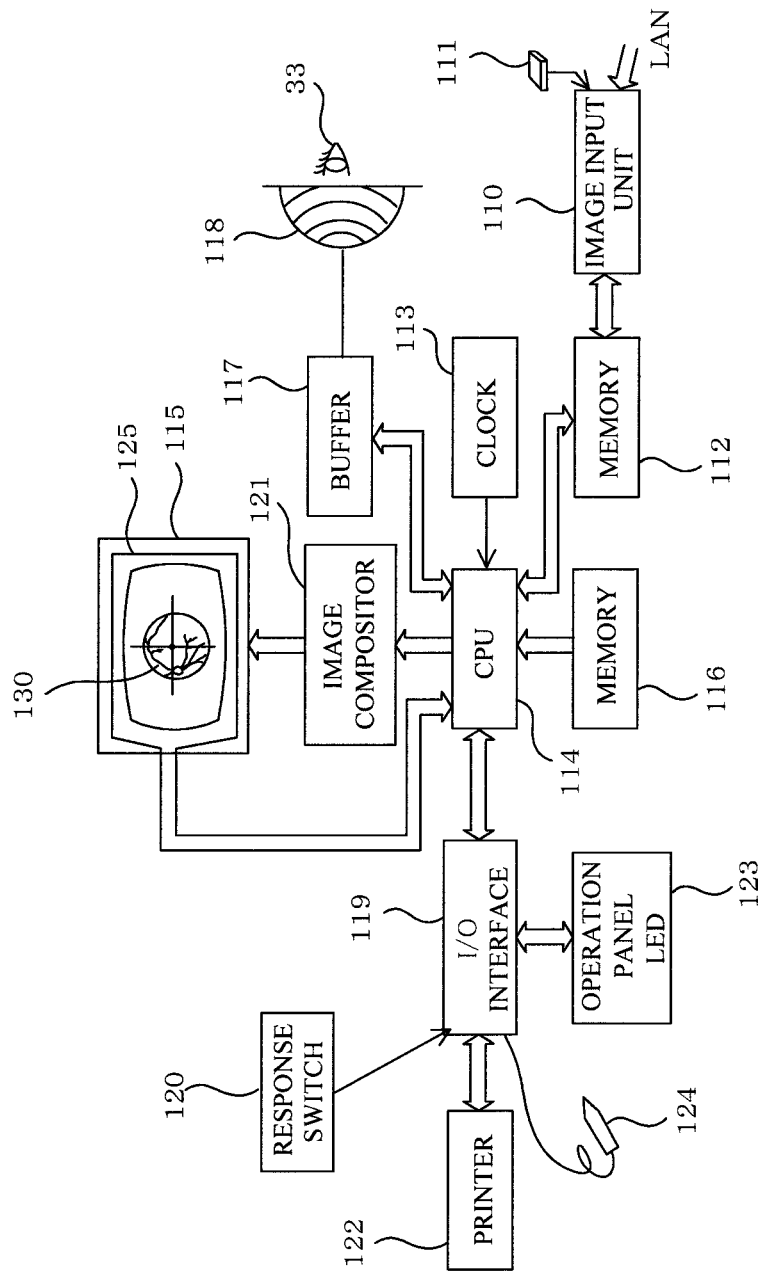
FIG. 2 is a block diagram illustrating one embodiment of a perimeter in the present invention.

FIG. 1 illustrates a configuration of an OCT fundus device used in the visual field examination system of the present invention, and FIG. 2 illustrates a configuration of a perimeter used in the visual field examination system of the present invention.

In FIG. 1, reference numeral 1 indicates a light source which is comprised of a super luminescent diode (SLD) for emitting partial coherent light, having the low-interference properties required in order to observe a tomographic image. The central wavelength is set so as to generate light in an infrared (non-visible) band such as, for example, 840 nm. A light beam from the light source 1 is collimated by a lens 2, and a light beam arriving via a mirror 3 is magnified to a light beam of a predetermined size via lenses 4, 5, and is then incident on a beam splitter 7 (BS; a light splitting member). At the position of the beam splitter 7, the optical path is split into four directions, namely, a light source-side optical path 6a, a reference optical path 6b, a probe optical path 6c, and a detection optical path 6d.

Provided further is a separate light source (not shown), e.g., an SLD or a laser diode (LD; a semiconductor laser) for emitting visible light (for example, red light of a wavelength of about 670 nm). A dichroic mirror or the like is used to align the optical axis of the separate light source with that of the light source 1. This makes it possible to utilize the separate light source as an auxiliary light source for confirming the optical paths of the non-visible infrared measurement rays using visible light.

A reference light mirror 9 reflects a light beam traveling the reference optical path 6b, and the light beam reflected by the reference light mirror 9 returns through the reference optical path 6b via a lens 8.

On the other hand, a light beam traveling the probe optical path 6c is incident on a galvano-mirror 10a mounted onto a galvanometer 10. The light beam reflected by the galvano-mirror 10a is reflected by a galvano-mirror 11a of a second galvanometer 11. Each of these two galvano-mirrors 10a and 11a allows the light beam to be scanned one-dimensionally in the direction orthogonal with respect to the optical axis.

For example, when one of the two galvano-mirrors 10a, 11a is fixed and the other is scanned, it is possible to scan the beam in the X-axis direction or Y-axis direction, which are perpendicular to the optical axis (the Z-axis). In the case of FIG. 1, for example, scanning in the X-axis direction can be carried out with the galvanometer 11 and scanning in the Y-axis direction can be carried out with the galvanometer 10.

Alternatively, when the two galvano-mirrors 10a, 11a are both operated at the same frequency, and the waveform type, amplitude, phase, and the like for driving each one are set as appropriate, it then becomes possible to scan the beam in the XY-plane as desired, in the shape of a line or the shape of a circle and so forth. The galvano-mirrors 10a and 11a constitute first and second light scanning means for scanning respective light beams of probe light at the same frequency as that of a line sensor array constituting a spectrometer 21.

The light beams scanned by the galvano-mirrors 10a, 11a pass through lenses 12, 13, 14 and are then incident on an eye under examination 33 (anterior ocular segment 33a and fundus 33b), which is an object to be observed. The lenses 12, 13 constitute a focusing optical system that can be adjusted in accordance with the diopter scale (myopia, hyperopia or the like) of the eye under examination, and serve as focus adjusting means for shifting the focus position of a light beam in accordance with the optical properties of an object concerned. The positions of the lenses 12 and 13 can be adjusted in the optical axis direction in accordance with the operation of a predetermined mechanism (not shown). The lenses 12, 13 and the lens 14 constitute a telecentric optical system, and are configured so that the conjugate relationship between the galvano-mirrors and the eye under examination is held substantially constant.

A light beam incident on the eye under examination 33 converges to a point and becomes in focus at a predetermined position of the fundus 33b. This light beam focused to a point scans the fundus 33b of the eye under examination in a line shape (or in a circle shape) by the scanning of the galvano-mirrors 10a, 11a (light scanning means).

Reflected light from the fundus 33b of the eye under examination 33 travels the optical system described above in reverse, i.e., passes through the lenses 12, 13, 14 and the galvano-mirrors 10a, 11a and returns to the beam splitter (BS) 7. The reflected light from the eye under examination 33 that traveled the probe optical path 6c in reverse and passed through the beam splitter 7 is composited with the reference light returned from the reference optical path 6b to generate coherent light on the detection optical path 6d.

The coherent light passes as detection light through a detection opening (a pin-hole) 17 via a lens 16, and further passes through a lens 18 on a diffraction grating 19 that is arranged so as to be at an incline with respect to the optical axis. The detection light arriving via the diffraction grating 19 is detected via a lens 20 by the spectrometer 21, which comprises a line sensor array.

A fast Fourier transformer (FFT) 22 converts an output signal of the spectrometer 21 to a spectral distribution signal, which is then inputted to a personal computer (PC) 23.

In the PC 23, information relating to the detection light inputted from the fast Fourier transformer 22 can be image-processed to detect the three-dimensional distribution of the biological components of the eye under examination.

The PC 23 controls the overall operation of the optical system (in particular, the two galvanometers 10, 11 and the like), and also displays a measurement result with respect to the three-dimensional distribution of tissue of a measurement target within the eye under examination on a display device 15 such as a liquid crystal television monitor. The PC 23 also causes the measurement result to be transferred to and stored in a memory 25, as needed. The PC 23 has a keyboard and/or pointing device (a mouse or the like), and can carry out settings for measurement control using these user interface means.

The memory 25, which is connected to the PC 23, has a first memory region and a second memory region used for the visual field examination, as described below. LAN or another communicating means is used to input to the PC 23 a two-dimensional fundus image of the eye under examination (that is, the same eye as the eye under examination 33) captured by a fundus image-capturing device such as a fundus camera (not shown).

In the present embodiment, for the sake of convenience, the PC 23 controls the visual field examination described below using an OCT image and a two-dimensional fundus image captured by the fundus image-capturing device. A visual field examination controlling means such as the PC 23 may also be arranged anywhere within the system; for example, the aforementioned fundus image-capturing device or a control unit of a perimeter described below may constitute the visual field examination controlling means.

The pin-hole 17 provided inside the optical system has a detection opening in a predetermined pin-hole shape that is limited in clearance in the scanning direction of the light scanning means. The pin-hole 17 removes noise caused by unneeded stray light and scattered light to enhance the signal/noise (S/N) characteristics of the detected coherence signal, and reduces the light level of the background, thereby producing the effect of enhancing the gradation of a signal component in a video signal from an imaging element. The pin-hole 17 may be an opening of a very small square shape; it would also be possible to configure this opening by arranging two slit-shaped thin sheets in an orthogonal direction and superimposing the two sheets.

In the configuration described above, a light beam incident on the eye under examination 33 can be converged to a point and focused at a predetermined position of the fundus 33b to scan the fundus 33b of the eye under examination 33 in a line shape (or circle shape) using the galvano-mirrors 10a, 11a.

The OCT scan involves an A-scan in a depth (Z-axis) direction that is performed at a specific XY coordinate of the fundus 33b, and a B-scan in which the A-scan is sequentially carried out at a subsequent XY coordinate to scan the fundus 33b of the eye under examination 33.

The structure of the perimeter will be described referring to FIG. 2. In FIG. 2, the reference numeral 110 indicates an image input unit that receives via a flexible disc 111, a removable disc such as a CD, or a LAN a fundus image that is captured by the fundus image-capturing device and converted to an electronic image.

The fundus image is captured by the fundus image-capturing device (a fundus camera or the like) via a television camera (a CCD camera) and undergoes image processing. The processed image can either be saved in the flexible disc 111 or the like or inputted via a LAN or the like. The fundus image inputted to the image input unit 110, after having been stored in a memory 112, can be displayed on a display unit such as a monitor 115 via a CPU 114 that operates in synchronization with a clock 113.

Stored in a memory 116 is also a program for measuring the visual field. As shall be described below, a predetermined region of the fundus displayed on the monitor 115 is specified, and the CPU 114 causes stimulus to be displayed in sequential order on a visual field dome 118 via a buffer 117. The stimulus are displayed either by projecting the stimulus onto the visual field dome, or by activating a light source such as an LED provided to the visual field dome. The display of the stimulus is carried out in association with the specified fundus region portion. In a case where the subject has fixed the gaze onto the center of the visual field dome, the stimulus displayed are adjusted so as to be in focus on the specified region of the fundus.

In a case where the subject recognizes a stimulus being displayed on the visual field dome 118, the subject responds with a response switch 120, and the response is transmitted to the CPU 114 via an input/output (I/O) interface 119. The CPU 114 can process the visual field measurement result and display the same on the monitor 115. The CPU 114 is adapted to be able to composite images processed by the CPU and display them on the monitor 115 via an image compositor 121.

Connected to the I/O interface 119 is an operation panel 123 that is provided with a light source such as an LED and allows a variety of operations such as image input, visual field measurement, and image compositing to be performed. The operations performed can be transmitted to the CPU 114 via the I/O interface 119. A measurement result or the like, or an image to be displayed on the monitor 115 can be outputted to a printer 122 via the I/O interface 119. The reference numeral 124 refers to a light pen, which can be used to either set or specify a region of an image being displayed on the monitor 115, via a touch panel 125 installed on the monitor 115.

The visual field examination system can be configured so that the PC 23 and the monitor 15 of FIG. 1 fulfills the functions of the operation panel 123, the I/O interface 119, the CPU 114, the memories 112, 116, the buffer 117, the image compositor 121 and the monitor 115 with the touch panel 125.

With such a configuration, fundus image data is inputted to the image input unit 110 via the flexible disk, the LAN, or the like, is stored in the memory 112, and is thereafter displayed on the monitor 115 via the CPU 114. This state is shown in FIG. 3 in which a fundus image 130 is displayed on a screen 115a of the monitor.

The subject is asked to gaze on a stimulus projected onto a projection surface inside the visual field dome 118, and in a case where the subject is able to visually recognize same, a response is returned to an examiner by some appropriate method (operation of the response switch 120 or a response by voice).

Figure 3:
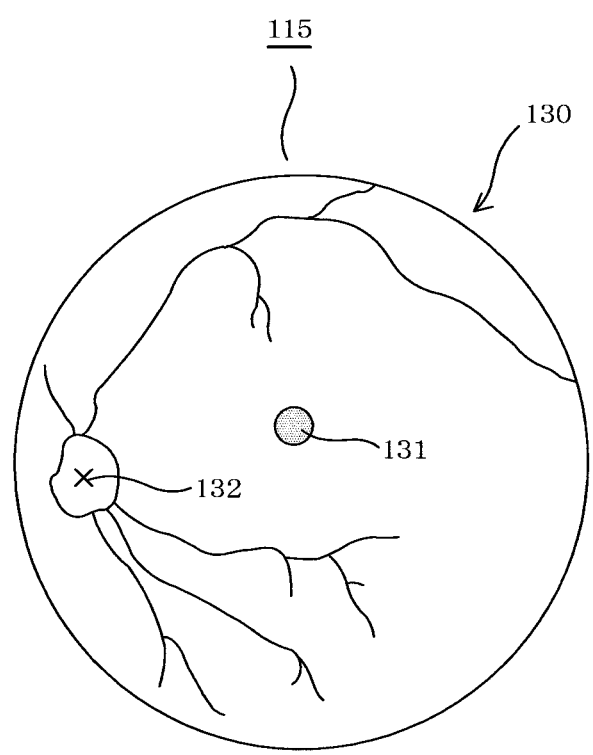
FIG. 3 is an illustrative view showing one example of a fundus image displayed on a monitor of a perimeter.

As illustrated in FIG. 3, the image 130 displayed on the monitor 115 is displayed with upside down for a case where an ordinary fundus image is displayed, and assumes a perimeter-compliant shape. In this state, the examiner uses the light pen 124 on the fundus image 130 displayed on the monitor 115 and specifies as a macula position K the center of a macula 131 serving as a visual field center (origin ZP), and also specifies the center position of a blind spot (optical nerve head) 132 as a blind spot position M11.

On the basis of the visual field measurement program stored in the memory 116, the CPU 114 detects and computes the coordinates of the macula position 131 and the blind spot position 132 that is specified on the monitor 115 using the light pen 124, and sets X-Y coordinates with the macula 131 as the origin thereof. Next, on the basis of the visual field measurement program, the CPU 114 provisionally determines that the blind spot position 132 specified on the monitor by the examiner is at X=−15° and Y=−3° on the basis of standard blind spot position coordinates data that is generally (statistically) presumed to be the blind spot position coordinates with respect to the macula 131. The CPU 114 then determines a scale for the X-Y coordinates in association with the blind spot position 132 and displays the same on the fundus image.

Figure 4:
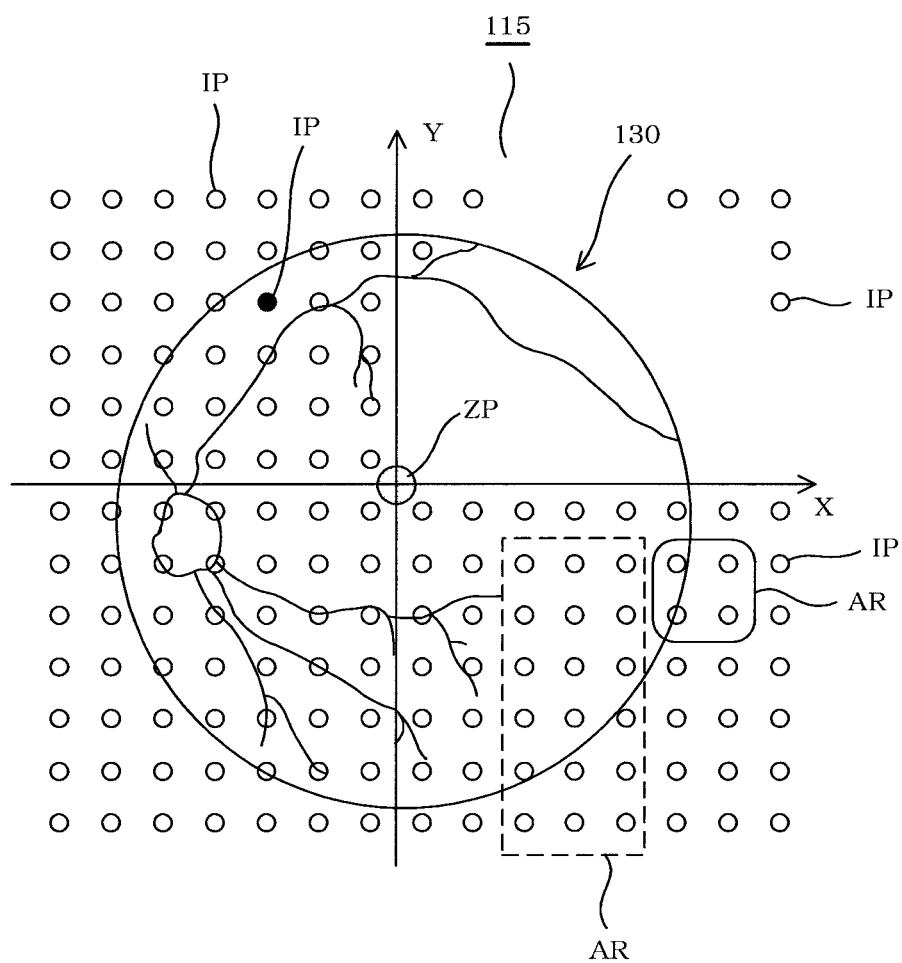
FIG. 4 is an illustrative view showing one example of a fundus image displayed on a monitor of a perimeter.

Next, on the basis of the visual field measurement program, the CPU 114, as illustrated in FIG. 4, displays on the monitor preset measurement points, i.e., examination points IP. The examination points IP thus displayed are set in, for example, the X- and Y-axis directions to an α and β at a view angle. The setting angles for α and β are as desired, but more specifically are set centered on the X- and Y-coordinate axis in a form that is divided by α/2 and β/2 and also at intervals of α and β that are equivalent in the X- and Y-axis directions. For example, the setting angles for α and β are set to about 4-5°.

For the sake of the diopter of the eye under examination, an insertion lens is used for an ocular lens (not shown) through which the subject peers in the perimeter. In such a case, the examiner inputs a correction value for the insertion lens via the operation panel 123. The CPU 114 adjusts the scale of the X-Y coordinates on the fundus image 130 in accordance with the inputted correction value for the insertion lens and corrects the coordinate axes. When the insertion lens is introduced, the recognition position of the stimulus in the visual field dome 118 deviates by, for example, 20% due to a prism effect by the insertion lens. In such a case, the scale of the X-Y coordinates on the fundus image 130 is corrected in accordance with the amount of this deviation.

In this state, the coordinate position is specified on the fundus image 130. This apparently allows the visual field coordinates to be determined within the visual field dome 118 for the eye under examination 33 peering into the corresponding visual field dome 118.

The examiner views the fundus image 130 and the examination points IP displayed on the monitor 115, and uses the light pen 124 or the like to specify on the screen of the monitor 115 points where the eye under examination 33 will be subjected to a visual field examination. As illustrated in FIG. 4, the images of the examination points IP are individually specified (for example, as the examination points IP illustrated with a black circle in FIG. 4), or a visual field examination region (AR) is specified in which one or more examination points IP to be examined are included. The examination point(s) IP to be examined can thus be specified while directly checking the fundus image 130 of the eye under examination 33 on the monitor 115. Therefore, the appropriate examination point(s) IP corresponding to the state of the eye under examination 33 can be easily selected.

Also, in the present embodiment, as shall be described below, it is possible to automatically generate the visual field examination region AR including a plurality of examination points IP on the basis of quantitative information relating to the three-dimensional structure of the retina acquired by OCT.

In the present embodiment in which the visual field examination utilizes the two-dimensional fundus image as described in FIGS. 2 to 4, the examination is further carried out using three-dimensional information on the fundus (retina) of the eye under examination 33 acquired with the OCT fundus device in FIG. 1.

Figure 6:
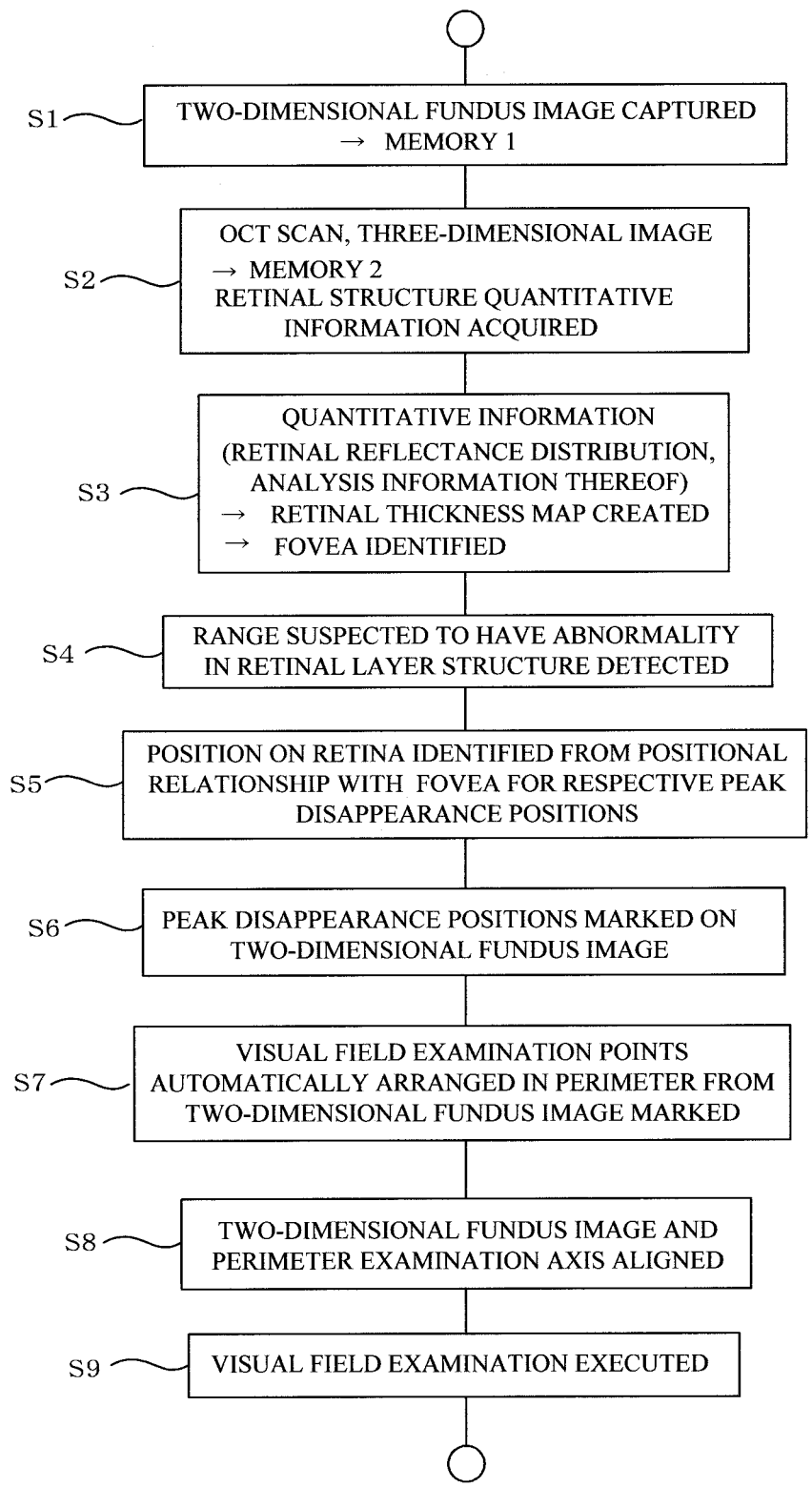
FIG. 6 is a flow chart illustrating a summary of an ophthalmologic examination procedure in the present invention.

FIG. 6 illustrates an examination control procedure in the visual field examination system of the present embodiment. The procedure depicted is executed as a control program for the visual field examination system by a system controller, e.g., the PC 23 in FIG. 1 (as described earlier, may also be executed by another control unit, e.g., a control unit of the perimeter in FIG. 2, or a control unit of the fundus image-capturing device). Procedures except for the examiner's operation or the subject's response are stored as a control program in a storing means such as a hard disk drive (HDD) of the PC 23.

When performing a visual field examination, the fundus image-capturing device such as fundus camera captures a two-dimensional fundus image, and image data is stored in a first memory region (step S1 in FIG. 6). The first memory region is arranged, for example, within the memory 25 of the OCT fundus device in FIG. 1, but may also be arranged within another memory, e.g., within the fundus image-capturing device or the memory 116 of the perimeter.

Next, three-dimensional image data of the retina is acquired by the OCT fundus device and stored in a second memory region (step S2), and then quantitative information of the three-dimensional retinal layer structure is acquired as well (step S3). The second memory region is arranged, for example, within the memory 25 of the OCT fundus device in FIG. 1, but may also be arranged within another memory, e.g., within the fundus image-capturing device or the memory 116 of the perimeter (step S2).

Herein, the phrase "quantitative information of the three-dimensional retinal layer structure" refers to the reflectance distribution of the retina obtained by the OCT fundus device and information derived from the analysis thereof. The OCT fundus device is a device that measures reflectance and depicts a three-dimensional structure, and is therefore able to analyze whether or not there is a peak in a reflectance distribution curve.

In step S3, in order to identify the position of the fovea, a retinal thickness map is created from the acquired quantitative information of the retinal layer structure. Close to the fovea, the retinal thickness becomes thinner, and therefore it is possible to identify to which position in the retinal thickness map the fovea corresponds. Herein, a three-dimensional structure of the retina of the eye under examination 33 can be displayed and outputted on the basis of the retinal thickness map thus created.

For example, a display could be produced with the monitor 15 (or 115) as a 3D image of a wireframe representation. This type of 3D image (three-dimensional) display may be performed using a user interface such as for rotating, enlarging, compressing, or the like by, for example, a keyboard or pointing device operation.

Figure 5:
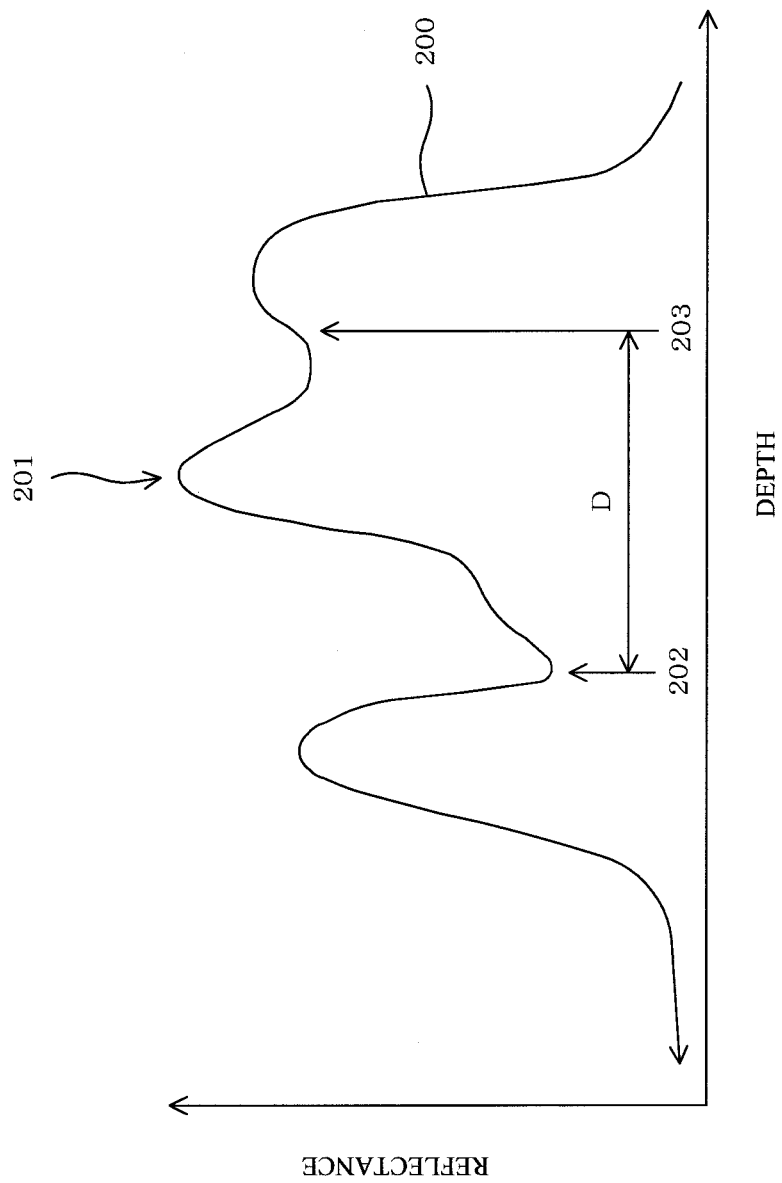
FIG. 5 is a graphic diagram for calculating a retinal thickness from an A-scan signal obtained by OCT.

The three-dimensional retinal layer structure undergoes a variety of analyses to detect a range suspected to have an abnormality (step S4). For example, for a normal eye, the reflectance distribution in the depth direction that is obtained in a certain scan according to the A-scan signal of the OCT is known to have several peaks of high reflectance, as in FIG. 5. In FIG. 5, the reference numeral 202 corresponds in particular to the nerve fiber layer (NFL) of the retina of specific positions in the retinal tissue of the eye under examination, and the reference numeral 203 corresponds to the posterior edge at the retinal pigment epithelium (RPE). The distance between 202 and 203 corresponds to the retinal thickness D.

In particular, there may be a position at which a peak corresponding to the junction between the inner segments and outer segments (IS/OS) of the photoreceptor cells, illustrated by the reference numeral 201, disappears over a specific range (or in a case where such a scan signal is obtained at certain XY coordinates). In such a case, photoreceptor cells at this position are suspected of possibly experiencing a failure. Detected in step S4 is thus a range suspected to have an abnormality in the retinal layer structure, which can be determined to be a peak disappearance position.

For each detected peak disappearance position, it is identified from the positional relationship with the fovea identified in step S3 to which position on the retina it corresponds (step S5).

Next, the position identified in step S5 is projected and marked on the two-dimensional fundus image that is acquired in step S1 and stored in the first memory region (step S6). At this time, the position (XY coordinates) acquired from the A-scan signal of the OCT at which an abnormality was detected is used to determine the position (XY coordinates) to be marked on the two-dimensional fundus image as a position suspected to have an abnormality.

At this time, in step S6, in the coordinate system of the two-dimensional fundus image, the fovea of the OCT image identified in step S3 is caused to coincide with the fovea detected in the two-dimensional fundus image, and necessary scale modifications are carried out to mark the same position of the coordinate system. In this manner, for example, the fovea in two images can be identified, and the positions thereof are used as a reference for alignment and scaling of both the OCT image and the two-dimensional fundus image. For the reference for the alignment between the OCT image and the two-dimensional fundus image, it would also be possible to identify the position not only of the fovea of the fundus, but also of the optical nerve head, the macula area, or the like, and to utilize the positions of these areas in both the images.

In step S6, the marked two-dimensional fundus image could simultaneously be displayed on the monitor 15 (FIG. 1) or 115 (FIG. 2).

With the perimeter in FIG. 2, the two-dimensional fundus image marked in step S6 is inputted (for example, inputted via the LAN or the image input unit 110). The CPU 114 of the perimeter detects the marked region and automatically arranges visual field examination points (step S7). This processing corresponds to that for automatically arranging the visual field examination region AR comprising the plurality of examination points IP shown in FIG. 4. The examination point density of the examination points IP at this time can be set by an operation by the examiner. The examination point density may also be varied depending on the examination point position. For example, the examination point density may be selected so that the density is higher in a region closer from the center and the density is lower in a region farther from the center.

For the purpose of comparison, other points (for example, vertically symmetrical points for the visual field center or fovea) may also be automatically selected as the examination points IP.

As described in connection with FIGS. 2 to 4, the two-dimensional fundus image marked is aligned with the visual field examination axes (step S8), and, similarly to the prior art, automatic visual field examination is carried out using a perimeter (step S9). At this time, the subject is made to gaze fixedly on a point, and for every presentation with the stimulus inside the visual field dome 118, the subject is asked to use the response switch 120 and perform the associated action in a case where the stimulus is seen.

Thus, it is possible to appropriately control a perimeter-assisted visual field examination by using a two-dimensional fundus image and information relating to the three-dimensional structure of the fundus of the eye under examination obtained by OCT. In the present embodiment, a position suspected to have a lesion or abnormality can be identified by using information relating to the three-dimensional structure of the retina by OCT, i.e., information relating to the thickness direction of the retinal layers. Therefore, it is possible to accurately identify the visual field examination range on the fundus and to efficiently carry out a visual field examination for the range of the fundus of the eye under examination suspected to have an abnormality.

The present embodiment doesn't employ a configuration in which the OCT information is incorporated after the visual field examination is carried out, as is the case in Patent Document 1, but employs a configuration in which the information relating to the three-dimensional structure of the retina is acquired by OCT and the visual field examination range on the fundus is narrowed down. Therefore, it is possible to quickly and efficiently carry out the visual field examination on the range of the fundus of the eye under examination suspected to have an abnormality.

INDUSTRIAL APPLICABILITY

The present invention can be broadly implemented in visual field examination systems that are configured by combining a fundus image-capturing device such as a fundus camera, an OCT and an automatic perimeter.

KEY TO SYMBOLS

1 Light source
2 Lens
3 Mirror
4, 5 Lens
7 Beam splitter
8 Lens
10, 11 Galvanometer
10a, 11a Galvano-mirror
12, 13, 14 Lens
16, 18, 20 Lens 19 Diffraction grating
21 Spectrometer (line sensor array)
22 Fast Fourier transformer (FFT)
23 Personal computer (PC)
25, 112, 116 Memory
30 Lens
33 Eye under examination
111 Image input unit
114 CPU
115 Monitor
118 Visual field dome
130 Fundus image
133 Eye under examination

The invention claimed is:

1. A visual field examination system in which a stimulus is presented at a predetermined position of a visual field coordinate system set on a visual field dome to measure the visual field of an eye under examination, the visual field examination system comprising:
a first memory for storing a two-dimensional fundus image of the eye under examination;
a second memory for storing a three-dimensional image of the retina of the eye under examination, the three-dimensional image being acquired by an optical coherence tomography (OCT) device;
fovea identifying means for identifying a position of the fovea of the fundus of the eye under examination from quantitative information of a three-dimensional retinal layer structure and from the three-dimensional retinal layer structure, the quantitative information of the three-dimensional retinal layer structure being obtained by means for detecting a peak from the reflectance distribution of the retina obtained by analyzing the three-dimensional image of the retina, and by means for detecting from the reflectance distribution of the retina the disappearance of a peak corresponding to a specific position within the retinal tissue of the eye under examination and for detecting the range of disappearance thereof;
fundus image position identifying means for identifying, from the positional relationship between the three-dimensional retinal layer structure and the fovea identified by the fovea identifying means, to which range in the three-dimensional image of the retina the range of disappearance of the peak corresponds; and
marking means for marking a predetermined examination point on the two-dimensional fundus image stored in the first memory at a position corresponding to the range of disappearance of the peak identified by the fundus image position identifying means;
wherein a region marked by the marking means is detected to generate, on the basis of the position of the region marked, a visual field examination region including visual field examination points to be presented on the visual field dome, the visual field examination points of the visual field examination region being presented to the subject using the visual field dome to perform a visual field examination for the eye under examination;
wherein the marking means performs, in the coordinate system on the two-dimensional fundus image, a scale modification so as to align the fovea identified by the fovea identifying means with the fovea in the two-dimensional fundus image, and marks the same position in the coordinate system on the two-dimensional fundus image; and
wherein the peak is at a location that corresponds to junctions between inner and outer segments of photoreceptor cells in the retina of the eye under examination.

2. A visual field examination system in which a stimulus is presented at a predetermined position of a visual field coordinate system set on a visual field dome to measure the visual field of an eye under examination, the visual field examination system comprising:
means for acquiring quantitative information of a three-dimensional retinal layer structure by detecting a range in which a peak of a retinal reflectance distribution obtained by retinal optical coherence tomography (OCT) scanning is lost;
means for identifying a position of the fovea of the ocular fundus of the eye under examination on the basis of the acquired quantitative information of the three-dimensional retinal layer structure;
means for specifying in a two-dimensional ocular fundus image, on the basis of the identified position of the fovea, a location corresponding to a range in which the peak of the retinal reflectance distribution is lost;
means for marking on a region of the two-dimensional ocular fundus image the specified location corresponding to the range in which the peak of the retinal reflectance distribution is lost;
means for detecting a position of the marked region of the two-dimensional ocular fundus image; and
means for generating a visual inspection field region on the basis of the detected position of the marked region of the two-dimensional ocular fundus image, the visual field inspection region comprising visual field examination points that are presented to the eye under examination through the visual field dome for carrying out visual field examination of the eye under examination;
wherein the means for marking performs, in the coordinate system on the two-dimensional ocular fundus image, a scale modification so as to align the identified position of the fovea with the fovea in the two-dimensional ocular fundus image, and marks the same position in the coordinate system on the two-dimensional ocular fundus image; and
wherein the peak is at a location that corresponds to junctions between inner and outer segments of photoreceptor cells in the retina of the eye under examination.

3. A computer implemented method for a visual field examination system in which a stimulus is presented at a predetermined position of a visual field coordinate system set on a visual field dome to measure the visual field of an eye under examination, the computer implemented method comprising:
acquiring quantitative information of a three-dimensional retinal layer structure by detecting a range in which a peak of a retinal reflectance distribution obtained by retinal optical coherence tomography (OCT) scanning is lost;
identifying a position of the fovea of the ocular fundus of the eye under examination on the basis of the acquired quantitative information of the three-dimensional retinal layer structure;
specifying in a two-dimensional ocular fundus image, on the basis of the identified position of the fovea, a location corresponding to a range in which the peak of the retinal reflectance distribution is lost;
marking on a region of the two-dimensional ocular fundus image the specified location corresponding to the range in which the peak of the retinal reflectance distribution is lost;

detecting a position of the marked region of the two-dimensional ocular fundus image;

generating a visual inspection field region on the basis of the detected position of the marked region of the two-dimensional ocular fundus image, the visual field inspection region comprising visual field examination points configured points to be presented on the visual field dome; and presenting the generated visual field examination points to the eye under examination through the visual field dome and measuring the visual field of the eye under examination;

wherein the marking includes performing, in the coordinate system on the two-dimensional ocular fundus image, a scale modification so as to align the identified position of the fovea with the fovea in the two-dimensional ocular fundus image, and marking the same position in the coordinate system on the two-dimensional ocular fundus image; and wherein the peak is at a location that corresponds to junctions between inner and outer segments of photoreceptor cells in the retina of the eye under examination.

* * * * *